United States Patent [19]
Chung et al.

[11] Patent Number: 5,247,932
[45] Date of Patent: Sep. 28, 1993

[54] SENSOR FOR INTRAUTERINE USE

[75] Inventors: Christopher Chung, Pleasonton; Eric Johansson, Dublin; Carl Ritson, San Jose; Paul D. Mannheimer, Belmont, all of Calif.; Helen M. McNamara, Leeds, England

[73] Assignee: Nellcor Incorporated, Hayward, Calif.

[21] Appl. No.: 775,315

[22] Filed: Oct. 11, 1991

Related U.S. Application Data

[63] Continuation-in-part of Ser. No. 699,104, Apr. 13, 1991, abandoned, and a continuation-in-part of Ser. No. 685,414, Apr. 15, 1991, Pat. No. 5,218,962.

[51] Int. Cl.⁵ ............................................. A61B 5/00
[52] U.S. Cl. ..................................... 128/633; 128/642
[58] Field of Search ............... 128/633, 634, 664, 665, 128/642, 670, 698, 700

[56] References Cited

U.S. PATENT DOCUMENTS

| | | | |
|---|---|---|---|
| 3,326,207 | 6/1967 | Egan | 128/642 |
| 3,772,593 | 11/1973 | Sidhu . | |
| 3,851,641 | 12/1974 | Toole et al. . | |
| 4,649,924 | 3/1987 | Taccardi | 128/642 |
| 4,706,688 | 11/1987 | Don Michael et al. | 128/785 |
| 4,808,931 | 2/1989 | Ling . | |
| 4,873,986 | 10/1989 | Wallace | 128/670 |
| 5,109,849 | 5/1992 | Goodman et al. | 128/633 |

FOREIGN PATENT DOCUMENTS

WO91/07910  6/1991  PCT Int'l Appl. .

*Primary Examiner*—Lee S. Cohen
*Assistant Examiner*—Kevin Pontius
*Attorney, Agent, or Firm*—Townsend and Townsend

[57] ABSTRACT

A sensor placement and retention mechanism for use with fetal sensor sites beyond the user's reach are disclosed. The preferred embodiment of this invention is a fetal pulse oximetry sensor having an active face through which a light source and a light detector operate. The sensor includes a handle that facilitates placement of the active face at a sensor site in a preferred region beyond the transcervical region and beyond the reach of the user. A pair of electrodes—one disposed against the fetus' skin and one exposed to the amniotic fluid—are used to confirm that the sensor is firmly in place on the fetus. In an optional sensor retention feature, a self-inflating bladder presses the active face of the sensor against the fetus' skin to optically couple the sensor with the tissue at the sensor site.

22 Claims, 5 Drawing Sheets

SENSOR FOR INTRAUTERINE USE

CROSS REFERENCE TO RELATED APPLICATIONS

This application is a continuation-in-part of application Ser. Nos. 07/699,104 filed on Apr. 13, 1991, abandoned, and 07/685,414 filed on Apr. 15, 1991, now U.S. Pat. No. 5,218,962.

BACKGROUND

This invention relates generally to instruments used to measure or detect a condition of the fetus in utero and, in particular, to pulse oximeter sensors used to measure the blood oxygen saturation of the fetus during labor and delivery.

Pulse oximeters are typically used to measure various blood characteristics, including arterial blood oxygen saturation and pulse rate. Pulse oximetry sensors pass light through a portion of the patient's tissue and photoelectrically detect pulsatile changes in the absorption of the light by the tissue. The detected light is then used to determine the characteristic of interest.

Pulse oximetry sensors generally fall into two categories. Transmissive pulse oximetry sensors shine light through opposed blood perfused tissue surfaces, such as a finger or an ear, by disposing the light emitters and photodetectors on opposite sides of the tissue. Transflectance sensors, on the other hand, emit light into and detect light from the same side of the tissue.

The quality of the optical signal generated by the pulse oximeter sensor depends on the quality of optical coupling between the sensor and the patient. Optical coupling refers to a relationship between two objects permitting light to be transmitted from one object to the other. In the context of a pulse oximeter sensor and a patient, optical coupling refers to a relationship between the sensor and the patient permitting the sensor to transmit light into the patient's blood-perfused tissue and permitting a portion of the light to return to the sensor after passing through the tissue. The quality of the optical coupling is related to the amount of light emitted by the sensor that actually enters the patient's tissue and to the portion of the light received by the sensor that actually passed through the patient's blood-perfused tissue.

Tissue characteristics at the sensor site can affect the quality of the optical coupling between the sensor and the patient. For example, the presence of hair or mucous on the skin will attenuate the light transmitted into the tissue by the sensor.

In addition, the physical position and orientation of a sensor with respect to the patient's skin will affect the optical coupling of the sensor with the patient. An improperly applied sensor may permit some of the light from the emitters to shunt directly to the photodetector without passing through the patient's tissue. This latter problem is more prevalent with transflectance sensors than with transmissive sensors.

Pulse oximeters may be used to measure fetal blood oxygen saturation during labor and delivery. Since the accessible part of the fetus (usually the top of the head) does not offer opposed tissue surfaces for transmissive pulse oximetry, transflectance sensors are used. The use of transflectance sensors in the fetal environment presents some unique optical coupling problems, both as to tissue characteristics at the sensor site and as to retention of the sensor at the chosen site.

Prior art fetal pulse oximetry sensors were placed on the portion of the fetus showing through the dilated cervix (the "presenting part") or on the portion of the fetus within the uterus and adjacent to the cervix (the "transcervical region"). Sensors placed on the presenting part were typically attached by hooks inserted through the fetus' skin or by suction to retain the sensor in place. Sensors placed on the transcervical region were held in place by the pressure of the cervical wall against the fetus. While neither fetal tissue region could be seen by the user, both regions could be reached by the user's fingers to ensure that the sensor was firmly in place on the fetus to provide adequate optical coupling between the sensor and the tissue.

SUMMARY OF THE INVENTION

As discussed in copending patent application Ser. No. 07/598,850, filed Oct. 15, 1990, cervical pressure on the presenting part of the fetus creates local edema (caput) which can suppress the fetal pulse and make pulse oximetry readings unreliable. In addition, the amplitude of the pulse in the presenting part and in the transcervical region can diminish as the cervix dilates.

During the periodic contractions of the uterine wall, additional local forces on the presenting part and the transcervical region are exerted actively by the cervix and passively by the mother's pelvic bones. These transient local forces may further affect pulse amplitude. Thus, obtaining strong and consistent pulses throughout labor and delivery may be difficult.

The readings may also be affected by fetal hair at the sensor site. Depending on its color and amount, hair attenuates the light to various extents. Hair also may cause light to be shunted from the light source to the light detector. The light attenuation and light shunting diminish the quality of the optical coupling between the sensor and the fetus.

To overcome some of these drawbacks to the placement of fetal sensors on the presenting part and the transcervical region, a transflectance sensor may be placed on a portion of the fetus beyond the transcervical region on fetal tissue that provides better oximetry signal characteristics (the "preferred region"). Because this preferred region is beyond the user's reach, however, the user cannot confirm that the sensor has been properly placed against the fetal tissue surface. In addition, prior art hook and suction sensor retention mechanisms cannot be used for fear that the sensor might be placed on sensitive areas, such as the fetus' eyes.

This invention is a sensor placement and retention mechanism for use with fetal sensor sites beyond the user's reach. The sensor of this invention provides adequate optical coupling while minimizing the potential for damage to both fetus and mother. In addition, the pulse oximeter sensor of this invention has a contact signal for indicating when the face of the sensor is properly placed against the fetus' skin.

The preferred embodiment of this invention is a fetal pulse oximetry sensor having an active face through which a light source and a light detector operate. The sensor includes a handle that facilitates placement of the active face at a sensor site in a preferred region beyond the transcervical region and beyond the reach of the user. A self-inflating bladder presses the active face of the sensor against the fetus' skin to optically couple the sensor with the tissue at the sensor site. A pair of electrodes—one disposed against the fetus' skin and one exposed to the amniotic fluid—are used to confirm that the sensor is firmly in place on the fetus.

The invention is discussed in greater detail below with reference to the drawings.

BRIEF DESCRIPTION OF THE DRAWINGS

FIG. 9 is a cross-sectional view of an alternative embodiment of the sensor of this invention.

DETAILED DESCRIPTION OF THE PREFERRED EMBODIMENT

Figure 1:
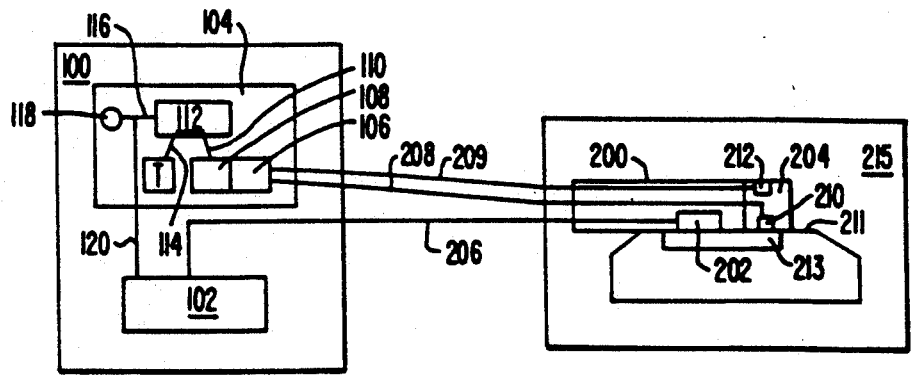
FIG. 1 is a block diagram of a fetal pulse oximetry system according to the preferred embodiment of this invention.

FIG. 1 is a block diagram of a fetal pulse oximeter system according to the preferred embodiment of this invention. The system includes a pulse oximeter sensor 200 comprising an optical signal unit 202 and a contact signal unit 204. Optical signal unit 202 may include a light source and a light detector in a manner known in the pulse oximetry art.

Contact signal unit 204 comprises a first electrode 210 adapted to be placed firmly against the surface 211 of the fetal skin when optical signal unit 202 of pulse oximeter sensor 200 is in place at the sensor site 213 in a manner that is likely to minimize the likelihood that light will shunt from the sensor's light source to the sensor's light detector (i.e., in a manner likely to maximize the quality of the optical coupling). Contact signal unit also comprises a second electrode 212 adapted to be exposed to the amniotic fluid 215 within the uterus when optical signal unit 202 is in place at the sensor site 213.

Optical signal unit 202 communicates via bus 206 with an oxygen saturation calculation unit 102 in a pulse oximeter monitor 100. Oxygen saturation calculation unit 102 may be configured in any manner known in the art, preferably as in the N-200 oximeter sold by Nellcor Incorporated.

Contact signal unit 204 communicates via buses 208 and 209 with a contact indicating unit 104 in oximeter monitor 100. Contact indicating unit 104 comprises a current generator 106 coupled to first electrode 210 via bus 208 and coupled to second electrode 212 via bus 209. Current generator 106 generates a current between first electrode 210 and second electrode 212.

Contact indicating unit 104 also comprises a voltage measuring unit 108 which (1) measures a voltage corresponding to the current flowing between first electrode 210 and second electrode 212 and (2) produces a measured voltage signal on a bus 110. The voltage received over bus 110 is directly proportional to the impedance of the electrical path between electrodes 210 and 212.

A comparator 112 receives the measured voltage signal from bus 110 and compares the received voltage to a threshold voltage value T received over a bus 114. Comparator 112 may be implemented entirely in hardware, or it may include an analog to digital converter and associated software.

Contact signal unit 204 and contact indicating unit 104 may be used to indicate whether sensor 200 is in proper contact with the fetal skin surface. As stated above, when optical signal unit 202 is properly in place against the fetal skin 211 at the sensor site 213, electrode 210 will be against the fetal skin 211, and electrode 212 will be exposed to the amniotic fluid 215. If, however, optical signal unit 202 is not firmly against the fetal skin (and is therefore not properly optically coupled with the fetus' tissue), both electrodes 210 and 212 will be exposed to the amniotic fluid surrounding the sensor. Since the impedance of the amniotic fluid 215 surrounding sensor 200 is lower than the impedance of the surface 211 of the fetal skin on which sensor 200 is placed, the voltage measured by voltage measuring unit 108 will be relatively high when electrode 210 is placed firmly against the fetal skin (i.e., when the electrical path between the electrodes crosses the fetal skin surface before reaching the amniotic fluid) and relatively low when both electrodes are exposed to the amniotic fluid (i.e., when the electrical path between the electrodes is an uninterrupted path through the amniotic fluid).

If threshold value T is chosen to be between the expected high and low voltage values, comparator 112 will provide a contact signal on a bus 116 to a contact indicator 118 indicating proper contact between first electrode 210 and the surface 211 of the fetal skin (and, hence, proper contact between optical signal unit 204 and the surface 211 of the fetal skin) when the voltage received over bus 110 is greater than the threshold value T received over bus 114. In addition, the contact signal may be sent over bus 120 to oxygen saturation calculation unit 102 to be used in the saturation calculation as discussed below with reference to FIG. 8.

Figure 2:
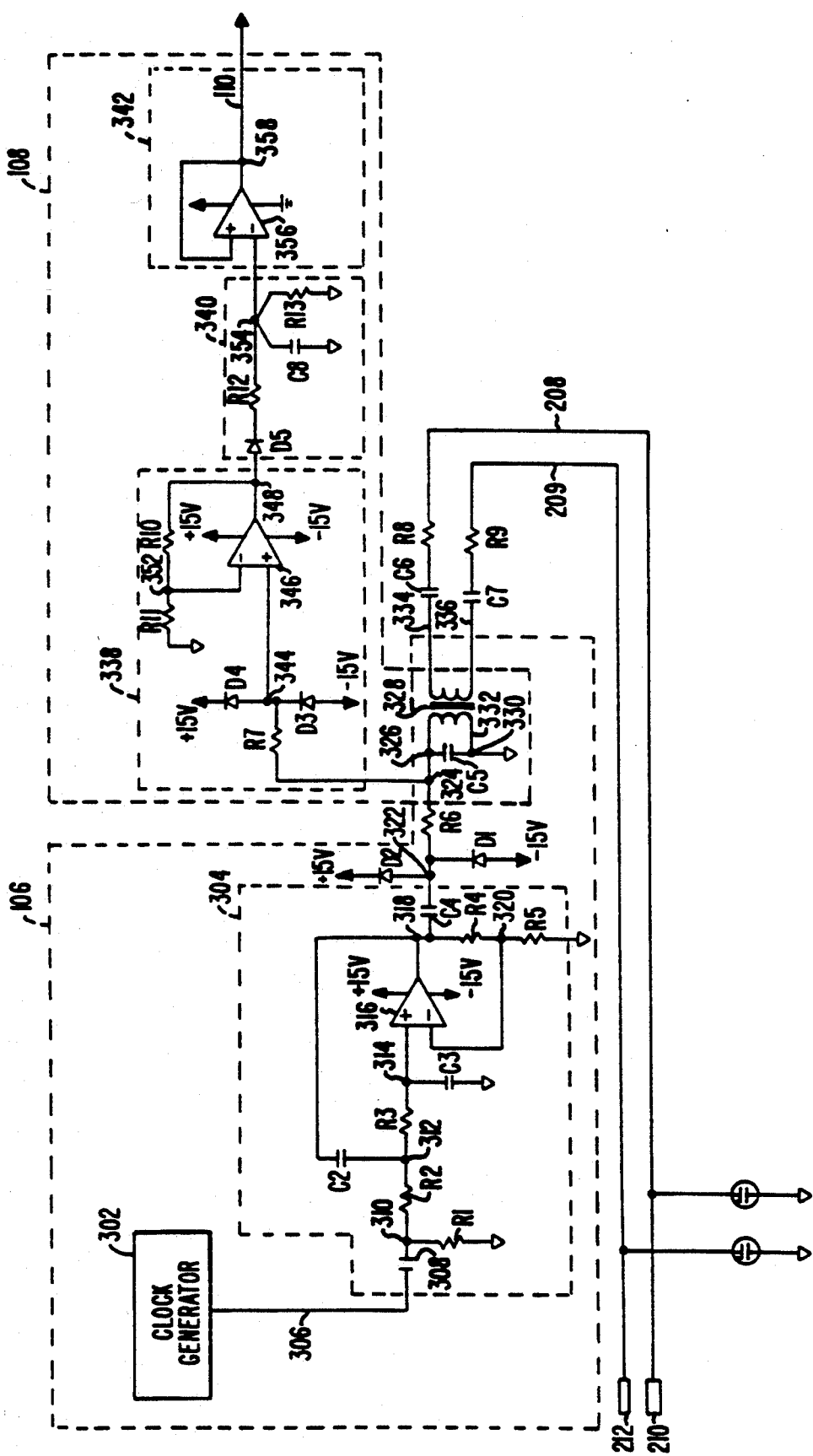
FIG. 2 is a schematic diagram of the current generator and voltage measuring unit of the sensor contact indicating system of this invention.

FIG. 2 is a schematic diagram of current generator 106 and voltage measuring unit 108 shown in FIG. 1. Current generator 106 comprises a clock generator 302 and a low pass filter 304. In this embodiment, clock generator 302 generates a 0-5 volt, 50 kHz square wave signal on a line 306 which is connected to one terminal of a capacitor 308 in low pass filter 304. The other terminal of capacitor 308 is coupled to a node 310 between a resistor R1 and a resistor R2. The other terminal of resistor R1 is coupled to a ground potential. The other terminal of resistor R2 is coupled to a node 312 between a resistor R3 and a capacitor C2. The other terminal of resistor R3 is coupled to a node 314 between the non-inverting input terminal of an operational amplifier (OP AMP) 316 and a capacitor C3. The other terminal of capacitor C3 is coupled to a ground potential. The output terminal of OP AMP 316 is coupled to a node 318 between an AC coupling capacitor C4, a resistor R4, and the other terminal of capacitor C2. The other terminal of resistor R4 is coupled to a node 320 between a resistor R5 and the inverting input terminal of OP AMP 316. The other terminal of resistor R5 is coupled to a ground potential. The other terminal of capacitor C4 is coupled to a node 322 between a current limiting resistor R6, the cathode of a diode D1 and the anode of a diode D2. The anode of diode D1 is coupled to a −15 volt power supply, and the cathode of diode D2 is coupled to a +15 volt power supply. The other terminal of resistor R6 is coupled to a node 324. The function of low pass filter 304 is to produce an approximately sinusoidal 50 kHz signal with a peak amplitude of approximately 5-6 volts at node 324.

Node 324 is coupled between one terminal of a resistor R7, one terminal of a high frequency filtering capacitor C5, and a first primary input terminal 326 of a transformer 328. The other terminal of capacitor C5 is coupled to a node 330 between a second primary input terminal 332 of transformer 328 and a ground potential. The signal at node 324 is thus applied across the primary input terminals 326, 332 of transformer 328. If current limiting resistor R6 has a value of approximately 100 kOhms, then the maximum current through the secondary side of transformer 328 is approximately 60 microamps.

A first secondary output terminal 334 of transformer 328 is coupled to bus 208 (and hence to first sensor 210) through a coupling capacitor C6 and a further current limiting resistor R8. Similarly, a second secondary output terminal 336 is coupled to bus 209 through a coupling capacitor C7 and a current limiting resistor R9.

Since the impedance across sensors 210 and 212 causes a voltage to be developed in response to the current flowing through secondary terminals 334 and 336 of transformer 328, and since this voltage is reflected across transformer 328 to primary input terminals 326 and 332 (and to node 324), then transformer 328 and node 324 may be considered a part of voltage measuring unit 108 as well as current generator 106.

Voltage measuring unit 108 comprises an amplifier 338, a peak detector 340, and a buffer 342. Amplifier 338 amplifies the voltage at node 324 by a factor of 3, and peak detector 340 senses and holds the peak voltage (positive or negative) output by amplifier 338 before communicating this voltage to buffer 342.

As mentioned previously, node 324 is coupled to one terminal of a resistor R7 which resides within amplifier 338. The other terminal of resistor R7 is coupled to a node 344 between the non-inverting input terminal of an OP AMP 346, the cathode of a diode D3, and the anode of a diode D4. The anode of diode D3 is coupled to a −15 volt power supply, and the cathode of diode D4 is coupled to a +15 volt power supply. The output terminal of OP AMP 346 is coupled to a node 348 between one input terminal of a resistor R10 and the anode of a diode D5 in peak detector circuit 340. The other terminal of resistor R10 is coupled to a node 352 between the inverting input terminal of OP AMP 346 and a resistor R11. The other terminal of resistor R11 is coupled to a ground potential. Node 348 provides the amplified voltage to peak detector 340.

The cathode of diode D5 is coupled to one terminal of a resistor R12. The other terminal of resistor R12 is coupled to a node 354 between the noninverting input terminal of an OP AMP 356 in buffer 342, one terminal of a capacitor C8, and one input terminal of a resistor R13. The other terminals of capacitor C8 and resistor R13 are coupled to a ground potential. The values of the foregoing components are chosen so that peak detector 340 may follow changing inputs on the order of several hertz.

OP AMP 356 forms buffer 342. The output terminal of OP AMP 356 is coupled to a node 358 between bus 110 and the non-inverting input terminal of OP AMP 356. Node 358 provides the voltage to be compared with the threshold voltage T in comparator 112.

Various modifications to the preferred circuit may be employed. For example, transformer 328 and its associated protection circuitry (e.g., the current limiting resistors) may be eliminated and the remaining current generating circuitry coupled directly to first sensor 210 and second sensor 212. Comparator 112 may be a window comparator which provides the contact signal only if the measured voltage is within a selected range, since a very high voltage may indicate that one of the sensors is disposed in air or against some other high impedance medium which is not of interest.

Figure 3:
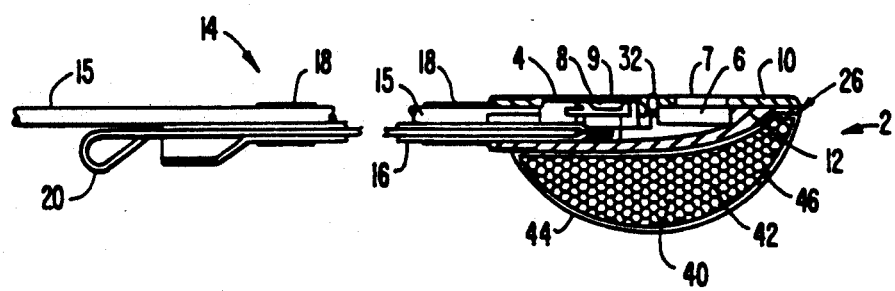
FIG. 3 is a cross-sectional view of a sensor according to the preferred embodiment of this invention.

FIG. 3 shows a side cross-sectional view of a sensor apparatus according to a preferred embodiment of this invention. Pulse oximetry sensor 2 comprises a two-piece resilient housing 4. Cover piece 10 is preferably formed of black silicone rubber and body piece 12 is formed from conductive black silicone rubber so that the sensor is able to bend a small amount longitudinally to conform to the shape of the site.

An electromagnetic radiation directing unit 6 and an electromagnetic radiation detecting unit 8 are disposed in the cover 10 of housing 4 to form the active face of the sensor. Radiation directing unit 6 comprises a first light emitting diode (LED) and a second LED (not shown). The first LED emits red light having a wavelength of approximately 660 nanometers (a red LED), and the second LED emits infrared light having a wavelength of approximately 900 nanometers (an infrared LED). Electromagnetic detecting unit 8 is a standard photodetector which may be shielded by a faraday shield to prevent electromagnetic interference. Radiation directing unit 6 and radiation detecting unit 8 are coupled to wires (not shown) which form a bus (corresponding to bus 206 shown in FIGS. 1 and 2) communicating with oxygen saturation calculating unit in a remote oximeter monitor (not shown). Any exposed parts of the wires may also be shielded by a grounded faraday shield. Clear silicone lenses 7 and 9 cover units 6 and 8, respectively.

An electrode 32 (corresponding to electrode 210 in FIG. 1) is disposed between units 6 and 8 in cover 10 of sensor housing 4. Electrode 32 is preferably formed from sterling silver, although other conductive materials may be used. Conductive silicone housing body 12 (which corresponds to electrode 212 of FIGS. 1 and 2) and electrode 32 are coupled to wires within cable 15 which form a bus (corresponding to buses 208 and 209 shown in FIGS. 1 and 2) communicating with a contact indicating unit in a remote oximeter monitor (not shown).

In an alternative configuration, the sensor body may be formed from a molded, opaque, flexible PVC or thermoplastic elastomer (such as polyurethane). Since these materials are not conductive, both electrodes would have to be separate conductive members disposed in the sensor body.

In addition, the optical components and the electrode on the active face of the sensor may be disposed on a standard fiberglass circuit board with conductive traces forming (in part) the buses communicating with the electrodes and optical components. In this embodiment, the electrode corresponding to electrode 212 of FIGS. 1 and 2 may be a conductive portion of the circuit board instead of a button electrode. The sensor body may be molded around the circuit board, with appropriate openings formed in the body for the electrodes and optical components.

Affixed to housing 4 of the preferred embodiment shown in FIG. 3 is a handle 14 which functions as an insertion and placement aid. Handle 14 comprises a substantially flat guide tube 16 which, together with the cable 15 containing the wires coupled to units 6 and 8, is enclosed by a tube 18 which may comprise heat shrink tubing. A removable stiffener 20 is disposed within guide tube 16 before shrinking tube 18. Stiffener 20 ensures that handle 14 has the desired property of allowing bending along the fetal head and the curve of the mother's pelvis toward the region to be probed while resisting lateral bending.

Figure 4:
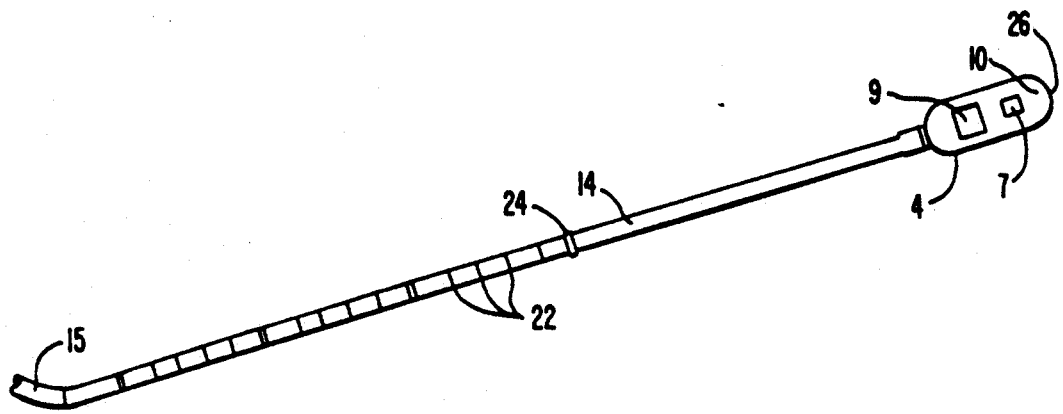
FIG. 4 is a front elevational view of the sensor shown in FIG. 3.

In the preferred embodiment, handle 14 has a series of regularly spaced markings 22, as shown in FIG. 4. These markings provide a visual indication of the insertion depth of the sensor in the mother's vagina. Markings 22 may also be used to gauge the descent of the fetus as labor progresses.

In addition, a ridge 24 may be formed on the handle at a predetermined distance from the leading edge 26 of the housing 4. The spacing between ridge 24 and the housing's leading edge 26 is such that, for the average fetus carried to term, housing 4 is in the preferred monitoring region within the mother's uterus when ridge 24 is at the sagittal suture of the fetal head.

A biasing bladder 40 partially covers conductive housing body 12 to provide an optional sensor retention feature. Bladder 40 is made, e.g., of a resilient, open-celled polyurethane foam 42 surrounded by a silicone skin 44 in which a small opening 46 has been formed. Opening 46 allows the bladder to be flattened during insertion of the sensor, as discussed further below, by permitting the air or other fluid within foam 42 and skin 44 to escape when a force is applied to the exterior of bladder 40. The resilient foam 42 will re-expand as the exterior force decreases, thereby drawing fluid back into bladder 40 through opening 46. In this embodiment, opening 46 is approximately 0.050 inches, although the size of the opening may be varied to produce the desired rate of re-expansion of bladder 40. The function of bladder 40 is to press the active face of sensor housing 4 firmly against the fetus at the sensor site and to keep the sensor in place during the contractions associated with labor.

Alternatively, foam 42 may be replaced with a spring, a diaphragm, or other biasing mechanism. Also, a self-skinning foam may be used in place of the foam 42 and skin 44.

In another alternative embodiment, self-inflating bladder 40 may be replaced with a hollow, sealed bladder that may be selectively inflated with saline solution or another suitable fluid after the sensor has been inserted into the uterus. The selectively inflatable bladder may be provided with a mechanism for maintaining a predetermined bladder fluid pressure, such as a pressure regulating valve.

The preferred method of using the apparatus of FIG. 3 is as follows. The user determines the location of the fetal back and the height and orientation of the fetal head by abdominal examination of the mother. The user then makes a vaginal assessment of cervical status using the Bishop score. This score grades the cervix on five elements: dilatation, effacement, position, station (of the fetal head, i.e., above, below, or at the ischial spines), and consistency (firm, soft, etc.) The vaginal examination also may precisely confirm the position of the fetal head.

Figure 5:
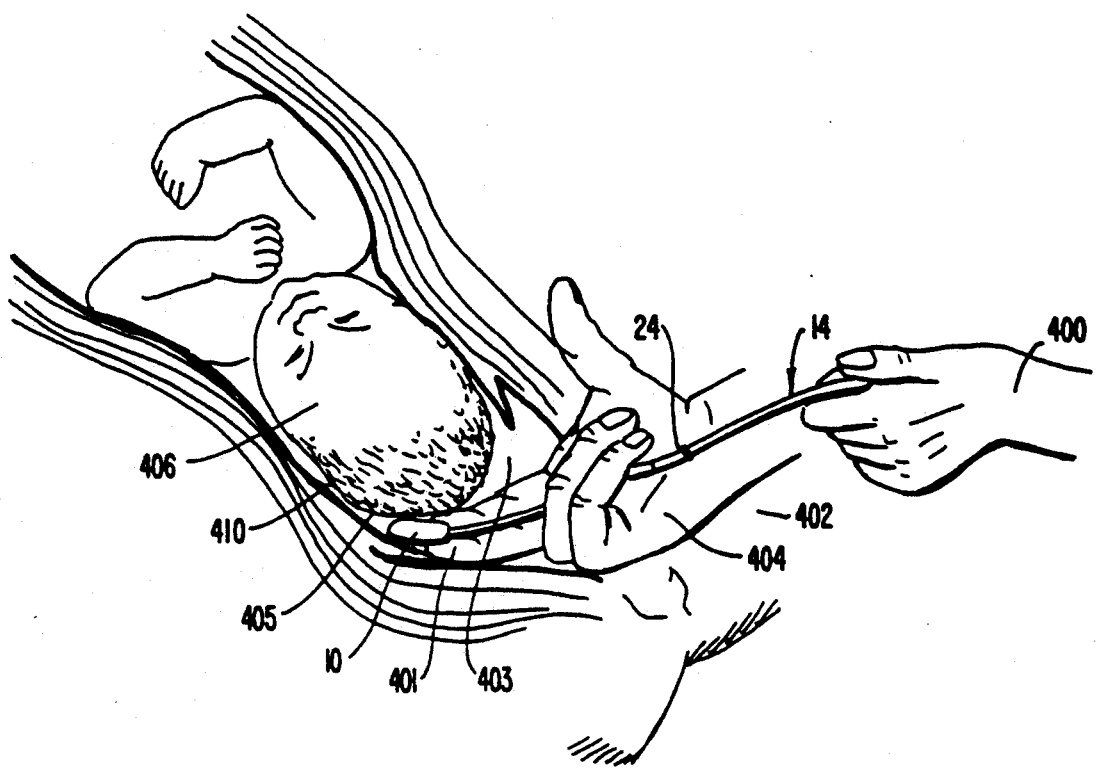
FIG. 5 is a diagram showing the user inserting a sensor into the vagina.
Figure 6:
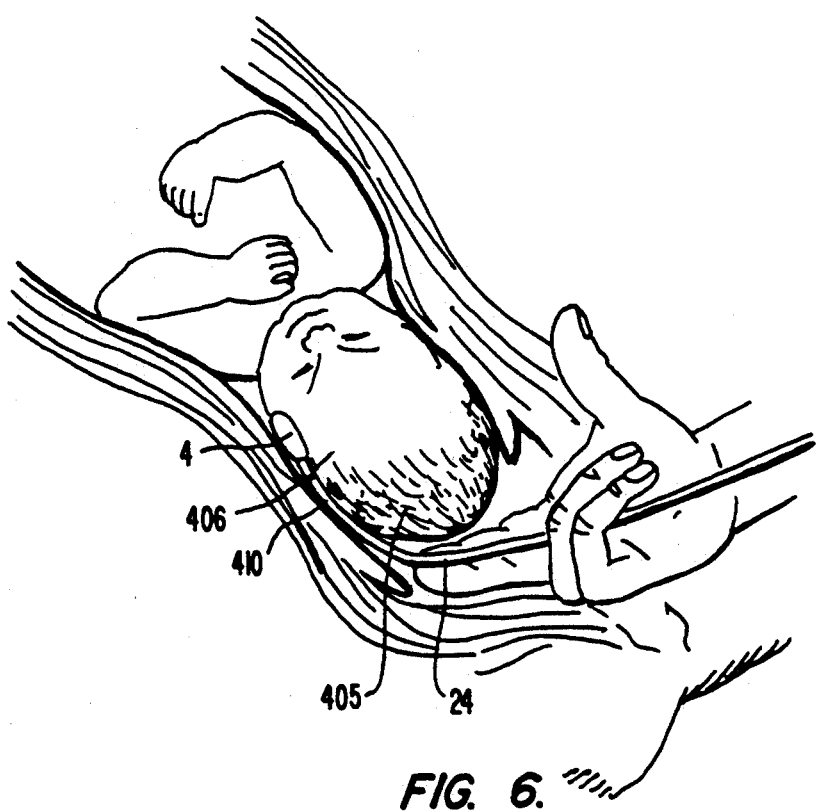
FIG. 6 is a diagram showing the user's hand guiding the sensor to the preferred region.
Figure 7:
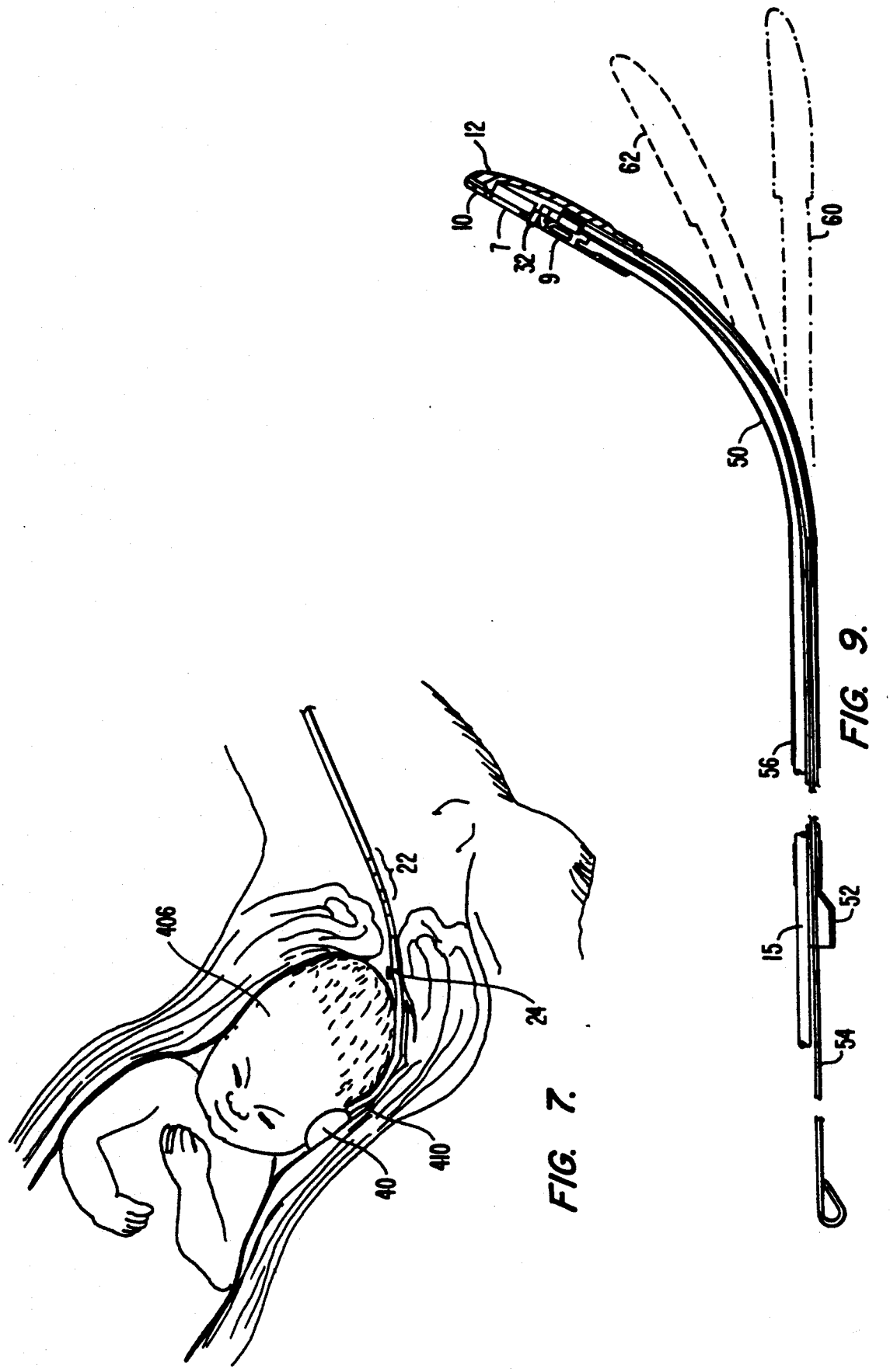
FIG. 7 is a diagram showing the sensor in place in the preferred region.

The preferred method of insertion and application of sensor 2 is shown in FIGS. 5-7. With the examining fingers 401 already in the vagina 402 and at the posterior cervix 403, the user grasps the apparatus by handle 14 with the other hand 400. Sensor housing 4 is inserted into the vagina with housing cover 10 faced toward the fetus. Sensor housing 4 is then threaded up between the index and middle fingers of the examining hand 404.

The fingers 401 of the examining hand stretch the posterior cervix 403 to make room for sensor housing 4. Pressure exerted by the cervix against the sensor compresses bladder 40. The user further advances sensor housing 4 into the uterus past the presenting part 405 and past the transcervical region, as shown in FIG. 6. Sensor housing 4 is then in the preferred region 406. For a fetus at term, ridge 24 on handle 14 will be flush with the vertex of the fetal head when the sensor housing 4 is in the preferred region 406, as shown in FIG. 7.

Bladder 40 will re-expand to fill the space between the uterine wall 410 and the fetus. The resilient force of bladder 40 will press sensor housing cover 10 (i.e., the active face of sensor 2 containing lenses 7 and 9 and electrode 32) firmly against the surface of the fetus' skin. This action by the bladder maximizes the quality of the optical coupling between the sensor and the tissue at the sensor site and helps retain the sensor at the sensor site in the preferred region 406 during labor and delivery.

In the preferred embodiment, a Nellcor Incorporated model N-200 pulse oximeter is modified to include the contact indicating unit 104 (i.e., the current generator, voltage measuring unit and comparator) of FIGS. 1 and 2. Electrode 32 and conductive sensor housing body 12 of sensor 2 connect to contact indicating unit 104 via wires disposed in sensor cable 15. Cable 15 connects to the N-200 pulse oximeter via a 9-pin connector.

In addition to retaining the sensor housing 4 at the chosen sensor site, the force between housing cover 10 and the resilient fetal skin created by the action of bladder 40 isolates electrode 32 from the amniotic fluid. Thus, the current generated by the current generator and flowing between electrodes 12 and 32 traverses the fetal skin as well as the amniotic fluid. In other words, the skin and amniotic fluid are resistors in series. The voltage measured by the oximeter's voltage measuring unit (i.e., element 108 in FIGS. 1 and 2) is therefore higher than the voltage that would have been measured if both electrodes were exposed to the relatively conductive amniotic fluid, in which case the amniotic fluid and skin would act as resistors in parallel (if the orientation of sensor 2 is such that electrode 32 is touching the skin and is also exposed to the amniotic fluid) or the amniotic fluid would act as a single resistor (if electrode 32 does not touch the skin at all). As discussed below, the voltage measuring unit will then send a signal to give a visual indication that the sensor is firmly in place. If the visual indicator fails to light, the user may move the sensor to an adjacent site in the preferred region in order to improve the contact between sensor and skin.

In an alternative embodiment, a plurality of interconnected electrodes may be used in place of electrode 32. For example, a pair of electrodes may be disposed laterally on the sensor's active face between the LEDs and photodetector. In this embodiment, the electrodes are electrically interconnected so that if either electrode is exposed to the amniotic fluid, the contact indicating unit will indicate that the sensor is not in place. Disposing the electrodes laterally helps ensure that the contact indicating unit will not indicate proper placement when the active face of the sensor is not flat against the fetus' skin but is rotated about the long axis of the sensor housing. Other electrode configurations are also possible.

Figure 8:
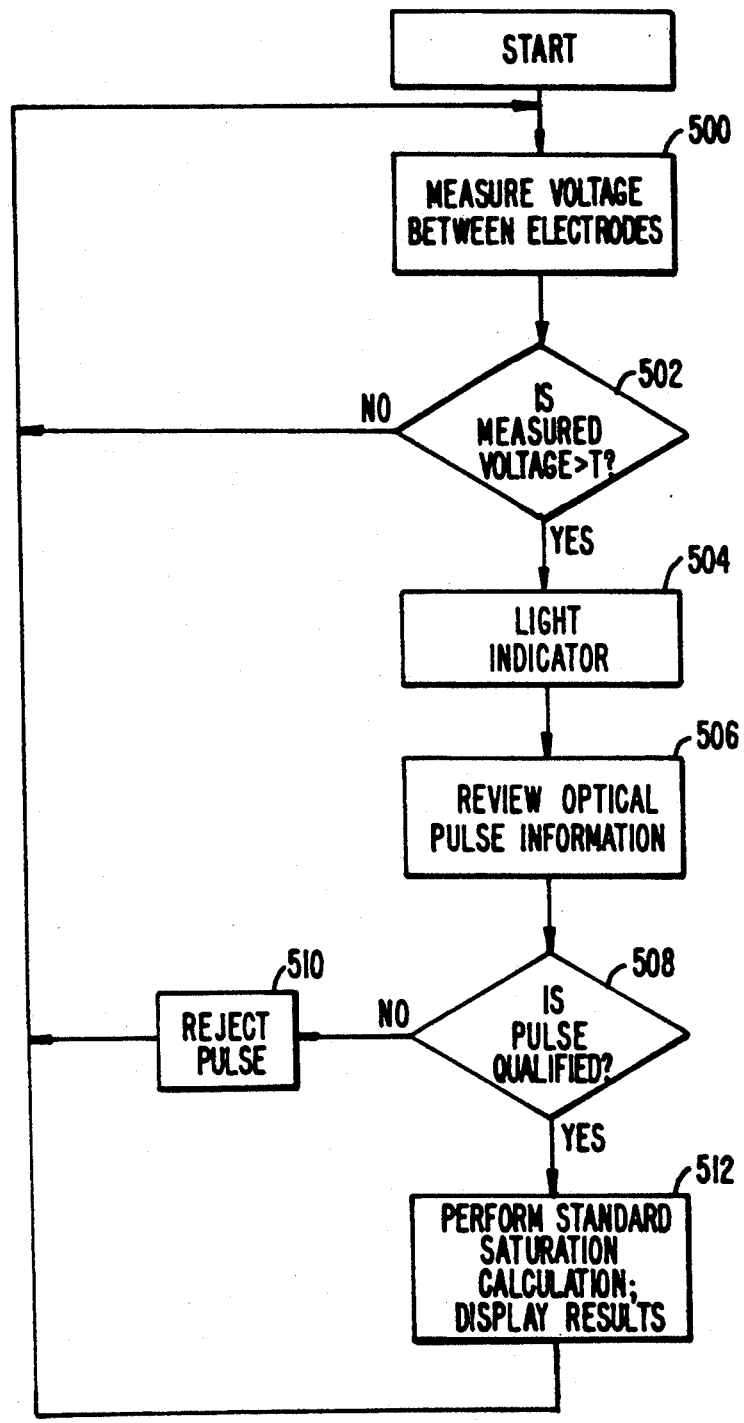
FIG. 8 is a flow chart showing the preferred method of using the contact indication signal.

The flow chart of FIG. 8 shows the preferred manner in which the measured voltage is used. Block 500 represents the measurement of the voltage between electrodes 12 and 32. Diamond 502 represents the comparison of the measured voltage with a predetermined threshold T. Threshold T is selected to be a value between the expected voltage when electrode 32 is in contact with the fetus' skin and the expected voltage when electrode 32 is away from the skin, i.e., when both electrodes are exposed to the amniotic fluid. Diamond 502 is a gate: if the measured voltage is not greater than the threshold T, oxygen saturation is not calculated.

If, however, the measured voltage is greater than T, an indicator lamp on the oximeter monitor is lit as represented by block 504, and the oximeter examines the most recent optical pulse data sent to its oxygen saturation calculation unit (i.e., element 102 of FIG. 1) by the sensor's photodetector 8 as shown by block 506. The oximeter's review of the optical pulse data preferably includes qualification of the most recent pulse with parameters such as (i) comparison with historical pulse amplitude, (ii) comparison with historical pulse frequency and (iii) correlation with an independent EGG signal.

As represented by diamond 508, if the pulse does not qualify, it is rejected. The algorithm then returns to block 500 and looks to see if the measured voltage still exceeds the threshold T. If the pulse meets the qualification criteria, however, the optical pulse is further processed and the saturation value is displayed in the manner of the prior art N-200 oximeter.

As an alternative to the "sensor contact" signal represented by block 504 in FIG. 8, the voltage measured by the voltage measuring unit can be used to generate a "no sensor contact" signal when the voltage is below the threshold. Also, the desired threshold value T may be coded into the sensor itself in a manner known in the art. The oximeter monitor would then be provided with means to read the threshold value from the sensor for use by the contact indicating unit.

FIG. 9 shows an alternative embodiment of the pulse oximeter sensor according to this invention. This embodiment omits the biasing bladder 40 of the embodiment of FIG. 3. Instead, sensor 2 has a curved handle 50. Handle 50 comprises a fixed curved sleeve 52 and an oppositely curved removable stiffener 54, both enclosed by a tube 56. Curved sleeve 52 and removable stiffener 54 are preferably formed from 0.020 inch and 0.025 inch stainless steel, respectively. Tube 56 has the same markings and ridge as the embodiment shown in FIGS. 3 and 4.

The spring constants of curved sleeve 52 and removable stiffener 54 are chosen so that the handle is substantially straight when stiffener 54 is in place. With stiffener 54 removed, i.e., in the sensor's relaxed state as shown in FIG. 9, the radius of handle 50 corresponds to one-half the radius of the head of a fetus at term. Inserting stiffener 54 straightens handle 50 (as shown in phantom outline 60 in FIG. 9) to facilitate insertion of the sensor housing into the uterus.

After insertion of the sensor housing the required depth into the uterus, straightener 54 is withdrawn. Since the radius of curvature of the fetus' head is greater than the radius of curvature of the sensor in the relaxed state, the sensor will be in the position shown in phantom outline 62, and the spring force of curved sleeve 52 will press cover 10 of sensor housing 4 (i.e., the active face of the sensor containing lenses 7 and 9 and electrode 32) against the surface of the fetus' skin. Because the handle's continuous curve helps the sensor housing conform to the shape of the fetus' head, this action optically couples the sensor's LEDs and photodetector with the tissue at the sensor site and helps keep the sensor in place at the sensor site during labor and delivery.

In an alternative embodiment, the shape and/or spring characteristics of the removable stiffener can be chosen so that the handle is slightly curved even with the stiffener in place within the handle. The initial curve could help insertion of the sensor by approximating the pelvic curve of the mother. Upon withdrawal of the stiffener in this embodiment, the sensor would assume the position shown in phantom outline 62 in FIG. 9.

Other modifications may be made to the disclosed apparatus and method without departing from the scope of the invention. For example, other sensor retention mechanisms, such as natural or applied suction, may be used in place of, or together with, the bladder or curved handle described above.

In addition, other uses may be made of the contact signal from the comparator of the contact signal unit. For example, the contact signal may be used as a gate for the oximeter's audible beep tone. Alternatively, the absence of a contact signal (or presence of a "no contact" signal) may sound an audible alarm.

Also, the sensor may be provided with a movable articulated handle whose position and shape may be controlled from a remote location outside the uterus.

In other embodiments of this invention, the sensor handle may be provided with a channel to provide access for a tool used to rupture the amniotic membranes and for the introduction of other transducers, such as an intrauterine pressure transducer.

Other modifications of the invention will be apparent to those skilled in the art.

What is claimed is:

1. A pulse oximetry apparatus for use in measuring a blood characteristic in fetal tissue during labor and delivery, the apparatus comprising:
   a sensor having an active face including a light source and a light detector;
   a handle means attached to said sensor for accurately placing the active face of the sensor on a site on a fetus beyond the presenting part and beyond the transcervical region; and
   a self-inflating bladder means attached to said sensor for retaining the active face of the sensor in place on the site on the fetus.

2. The apparatus according to claim 1 wherein the bladder means has a compressible, self-expanding, foam disposed therein for inflating the bladder means.

3. The apparatus according to claim 1 wherein the bladder means has an opening disposed on a surface thereof for controlling the rate of self-inflation of the bladder means.

4. The apparatus according to claim 3 wherein the opening is approximately 0.050 inches.

5. A pulse oximetry apparatus for use in measuring a blood characteristic in fetal tissue during labor and delivery, the apparatus comprising:
- a sensor having an active face including a light source and a light detector;
- a handle means attached to said sensor including a sleeve having a predetermined radius of curvature for accurately placing the active face of the sensor on a site of a fetus beyond the presenting part and beyond the transcervical region; and
- a rod removably insertable into the sleeve, the rod being constructed so that the radius of curvature of the sleeve is altered when the rod is inserted into the sleeve.

6. The apparatus according to claim 5 wherein the rod is constructed so that the radius of curvature of the sleeve increases when the rod is inserted into the sleeve.

7. The apparatus according to claim 6 wherein the rod is constructed so that the sleeve is substantially straight when the rod is inserted into the sleeve.

8. The apparatus according to claim 7 wherein the sleeve comprises approximately 0.020 inch steel, and wherein the rod comprises approximately 0.025 inch steel.

9. A pulse oximetry apparatus for use in measuring a blood characteristic in fetal tissue during labor and delivery, the apparatus comprising:
- a sensor having an active face including a light source and a light detector;
- a handle means attached to said sensor for accurately placing the active face of the sensor on a site of a fetus beyond the presenting part and beyond the transcervical region; and
- contact determining means for determining whether the active face is placed firmly in contact with the site on the fetus, the contact determining means including:
  - a first electrode disposed on the active face of the sensor;
  - a second electrode; and
  - current generating means for generating current between the first electrode and the second electrode.

10. The apparatus according to claim 9 wherein the second electrode is located on a surface of the sensor other than the active face of the sensor.

11. The apparatus according to claim 10 wherein the second electrode is located on a surface of the sensor opposite the active face of the sensor.

12. The apparatus according to claim 9 wherein the contact determining means further comprises impedance measuring means, coupled to the current generating means, for measuring the impedance between the first electrode and the second electrode in accordance with the current flowing between the first electrode and the second electrode.

13. The apparatus according to claim 12 wherein the contact determining means further comprises threshold comparing means, coupled to the impedance measuring means, for comparing the measured impedance to a threshold value.

14. The apparatus according to claim 13 wherein the contact determining means further comprises contact indicating means, coupled to the threshold comparing means, for providing a signal when the measured impedance exceeds the threshold value for indicating that the active face is placed firmly in contact with the site on the fetus.

15. The apparatus according to claim 14 wherein the contact indicating means comprises a visual indicator that is activated when the measured impedance exceeds the threshold value.

16. The apparatus according to claim 14 further comprising:
- calculating means for calculating a blood oxygen saturation value;
- signal communicating means, coupled to the light detector and to the calculating means, for communicating signals corresponding to optical data from the light detector to the calculating means;
- wherein the calculating means includes saturation calculating means for calculating a blood oxygen saturation value using the signals corresponding to the optical data; and
- wherein the saturation calculating means is coupled to the contact indicating means for altering the calculation of the blood oxygen saturation value in a predetermined manner when the active face is not placed firmly in contact with the site on the fetus.

17. A method of measuring a blood characteristic in fetal tissue during labor and delivery comprising the steps of:
- inserting a sensor into a mother's uterus, the sensor having an active face;
- placing the active face of the sensor on a site on a fetus beyond the presenting part and beyond the transcervical region;
- calculating the blood characteristic;
- determining whether the active face of the sensor is placed firmly in contact with the site on the fetus; and
- altering the calculation of the blood characteristic in a predetermined manner if the active face of the sensor is not firmly in contact with the site on the fetus.

18. The method according to claim 17 wherein the determining step comprises the step of causing current flow between a first electrode disposed on the active face of the sensor and a second electrode.

19. The method according to claim 18 wherein the determining step further comprises the step of measuring the impedance between the first electrode and the second electrode in accordance with the current flowing between the first electrode and the second electrode.

20. The method according to claim 19 wherein the determining step further comprises the step of comparing the measured impedance to a threshold value.

21. The method according to claim 20 wherein the determining step further comprises the step of providing a signal when the measured impedance exceeds the threshold value for indicating that the active face is placed firmly in contact with the site on the fetus.

22. The method according to claim 21 wherein the determining step further comprises the step of activating a visual indicator when the measured impedance exceeds the threshold value.

* * * * *